United States Patent [19]

Turchetta et al.

[11] Patent Number: 5,756,737
[45] Date of Patent: May 26, 1998

[54] PROCESS FOR THE PREPARATION OF 9-(2-HYDROXY)-ETHOXYMETHYL-GUANINE

[75] Inventors: Stefano Turchetta; Sabina Pucci; Gianfranco Piccoli; Giovanni Frare, all of Milan, Italy

[73] Assignee: Recordati S.A. Chemical and Pharmaceutical Company, Chiasso, Switzerland

[21] Appl. No.: 602,789

[22] PCT Filed: Feb. 3, 1994

[86] PCT No.: PCT/EP94/00308

§ 371 Date: Mar. 7, 1996

§ 102(e) Date: Mar. 7, 1996

[87] PCT Pub. No.: WO95/07281

PCT Pub. Date: Mar. 16, 1995

[30] Foreign Application Priority Data

Sep. 10, 1993 [IT] Italy ................... RM93A0608
Nov. 3, 1993 [IT] Italy ................... MI93A02324

[51] Int. Cl.[6] ................... C07D 473/18
[52] U.S. Cl. ................... 544/276; 544/251
[58] Field of Search ................... 544/276

[56] References Cited

U.S. PATENT DOCUMENTS

| 4,146,715 | 3/1979 | Schaeffer | 544/276 |
| 4,816,447 | 3/1989 | Ashton | 514/81 |

FOREIGN PATENT DOCUMENTS

| 0 532 878 | 3/1993 | European Pat. Off. |
| 59-80685 | 5/1984 | Japan |
| 1567671 | 5/1980 | United Kingdom |

OTHER PUBLICATIONS

Shapiro, Biochemistry 8, 238(1969).

Primary Examiner—Mark L. Berch
Attorney, Agent, or Firm—Griffin, Butler, Whisenhunt & Szipl

[57] ABSTRACT

A process for the preparation of acyclovir by alkylation of $N^2$-formylguanine with 2-oxa-1,4-diacyloxybutane and hydrolysis of the resulting intermediate is described.

7 Claims, No Drawings

PROCESS FOR THE PREPARATION OF 9-(2-HYDROXY)-ETHOXYMETHYL-GUANINE

This application is based on International Application No. PCT/EP94/00308, filed on Feb. 3, 1994 and published as International Publication No. WO 95/07281 on Mar. 16, 1995.

BACKGROUND OF THE INVENTION

The present invention relates to a novel, improved process for the preparation of 9-(2-hydroxy)-ethoxymethyl-guanine, of formula (I)

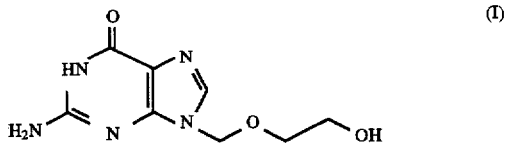

The preparation of compound (I), known as "acyclovir" and widely used in therapy as an antiviral, was described for example in Belgian Patent 833,006 starting from guanine, which is first subjected to trimethylsilylation at the three 2-amino, 6 and 9 positions. The resulting silylated intermediate is then treated with 2-benzoyloxyethoxymethyl chloride, to form (after deprotection of the $N^2$ and $N^6$ positions) 9-(2-benzoyloxy)ethoxymethyl-guanine, from which acyclovir is recovered by ammonolysis in methanol. The process involves the use of a very strong excess of the silylating agent, with obvious problems as far as costs and wastes are concerned, moreover it leads to a product which is remarkably impure for the presence of the 7-substituted isomer in unacceptable amounts in view of the pharmaceutical use.

British Patent 1,567,671 discloses another process, in which the protection of the amino group at the 2-position is carried out by acylation; the patent claims, as acylating groups, acetyl, propionyl, butyryl and benzoyl, even though the only described case is the one of $N^2$,9-diacetylguanine, which is reacted with 2-oxa-1,4-diacetoxybutane to give $N^2$-acetyl-9-(2-acetoxy)ethoxymethyl-guanine, which is hydrolysed to yield finally acyclovir, in yields which could be satisfactory if only remarkable amounts (up to 13%) of the 7-isomer did not form, which—besides forming to the detriment of the desired product—involves further expensive purification steps.

U.S. Pat. No. 4,146,671 provides a method for the preparation of guanine derivatives, including acyclovir, by reacting a diacylated guanine with a diester of 2-oxa-or 2-thiabutanediol and subsequent hydrolysis.

EP 0 532 878 describes the preparation of acyclovir starting from guanosine and a diester of 2-oxa-butanediol and acetic anhydride, followed by hydrolysis. The desired product is obtained together with the 7-isomer, which is to be converted into the desired 9-isomer.

SUMMARY OF THE INVENTION

Now it has surprisingly been found that acyclovir can be obtained in high yields, substantially preventing the undesired 7-isomer to form, by carrying out the alkylation of the 9-position of the purine ring with 2-oxa-1,4-diacetoxybutane on $N^2$-formylguanine. The latter compound is described in literature (Shapiro, Biochemistry, 8, 231–245 (1969)). According to this author, $N^2$-formylguanine can be obtained by treatment of the glyoxal-guanine adduct with sodium periodate and/or periodic acid. The process is reproducible in high yields, although $N^2$-formylguanine can be obtained, according to the process of the invention, also through other ways.

DESCRIPTION OF PREFERRED EMBODIMENTS $N^2$-formylguanine may also be obtained by the following:

oxidation of the glyoxal-guanine adduct by means of peracetic acid or hydrogen peroxide or lead tetraacetate;

direct formylation of guanine with formic acid, in the presence or not of solvents such as dimethylformamide or dimethylsulfoxide, optionally in the presence of dicyclohexylcarbodiimide;

direct formylation of guanine with formylacetic anhydride, optionally in solvents such as dimethylformamide, dimethylsulfoxide, hexamethylphosphoric triamide or formic acid.

Whichever operative procedure to prepare $N^2$-formylguanine is followed, the subsequent reaction of said compound with 2-oxa-1,4-diacetoxybutane leads, in yields above 90% (and, more significantly, with formation of only traces of the 7-isomer) to $N^2$-formyl-9-(2-acetoxy)ethoxymethyl-guanine, which is finally deacylated either in a single step, with aqueous alkali, or is first deformylated in acid medium and finally deacetylated by alkali hydrolysis. The following scheme summarizes the process according to the invention.

Scheme 1

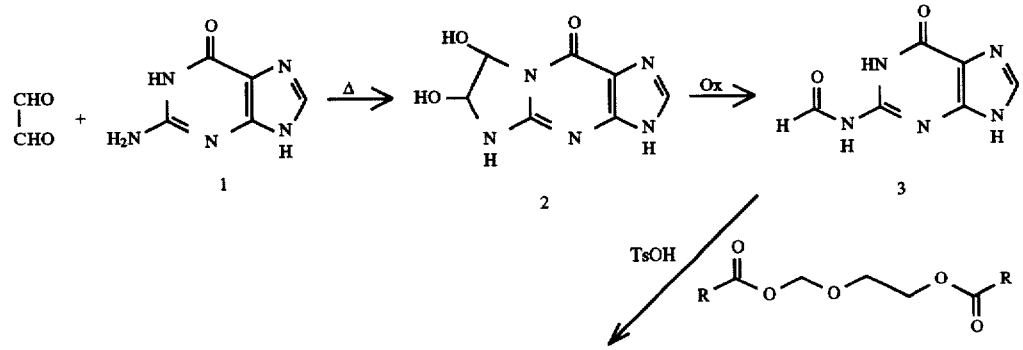

-continued
Scheme 1

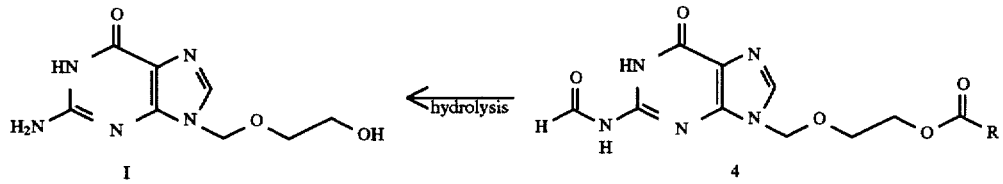

In said scheme R is hydrogen, $C_1$–$C_4$ alkyl or phenyl. The diol product (2) can be recovered in high yields suspending guanine (1) in $H_2O$, adding a glyoxal aqueous solution and heating the mixture to 80° C. for 4 hours (R. Shapiro, loc. cit; R. Shapiro and J. Hachmann, *Biochemistry* 5, 2799 (1966)). Diol (2) can then be oxidized to formyl derivative (3) in very good yields by means of a stoichiometric amount of $NAIO_4$ in water kept at pH 1.8–2.2.

$N^2$-Formylguanine (3) (which, as already stated, is obtainable also by direct formylation of guanine) can then be subjected to the alkylation reaction to obtain the N-9 alkylated compound (4) in high yields, without formation of the N-7 alkylated product in important percentages; finally acyclovir (I) can be obtained from compound (4) by hydrolysis with aqueous NaOH, in excellent yields.

On the whole, therefore, the above described synthesis allows to obtain the desired product (I) in quite satisfactory yields, higher than those obtained with the synthesis via acetylguanine, and above all without formation of noticeable amounts of the 7-alkylated product.

In a further embodiment, the process of the present invention provides a final purification step in order to obtain acyclovir substantially free from guanine. Said purification step advantageously provides acyclovir in very highly pure form.

It has been found that eluting an aqueous basic solution of acyclovir through a strong anionic ion exchange resin allows to obtain the desired product substantially free from guanine.

According to the present invention, the purification step comprises:

a) dissolving acyclovir into an aqueous basic solution and diluting the so obtained solution with water;

b) loading said diluted solution of point a) on a strong anionic ion exchanging column in a resin:acyclovir w/w ratio ranging from 2 to 1.5;

c) eluting said diluted solution at a flow ranging from 200 to 300 ml/hour;

d) eluting acyclovir with an eluant consisting of a mixture formed by lower alcohol/aqueous base solution in a v/v ratio ranging from 0.8 to 1.2, and with a eluant/acyclovir v/w ratio ranging from 15:1 to 20:1 l/kg at the same flow as point c) to give an eluate;

e) isolating acyclovir from said eluate of point d).

Anionic ion exchange resins are resins of the basic type, which consist of polymers having several crosslinking degrees and bearing quaternary ammonium groups. The resins used according to the present invention are basic resins of the strong type.

Examples of strong basic resins are dextrans, agarose, cellulose, divinylbenzene, appropriately functionalized with quaternary ammonium groups.

These resins are normally commercially available with the trade marks Amberlite®, Dowex®, Sephacel®, Sephadex®, etc.

Amberlite® IRA-400, Relite® 3A, IMAC HP-441 are preferred.

The chromatography is carried out on the resin in its basic form.

The elution is performed at room temperature.

The aqueous basic solution of point a) consists of an alkaline metal hydroxide, such as lithium, sodium, potassium hydroxide, solution. The base concentration ranges from 5 to 15%, a 10% sodium hydroxide solution being preferred.

A 1.75 resin:acyclovir w/w ratio is preferred.

The preferred eluant flow is 250 ml/hour.

Lower alcohols of point d) are methyl alcohol, ethyl alcohol, propyl alcohol. The aqueous base solution of point d) consists of an alkaline metal hydroxide in a concentration ranging from 0.8 to 1.2M., A 1:1 v/v methyl alcohol/1M sodium hydroxide is preferred.

A 17.5 l/kg eluant/acyclovir v/w ratio is preferred.

The isolation of the product from the eluate as in point e) is carried out according to conventional techniques. Preferably, acyclovir is precipitated by acidifying the eluate with an appropriate acid.

The so obtained product has a guanine content lower than 0.1%.

According to the purification step of the present invention, the so obtained acyclovir is from 3 to 4 times purer than the best commercially available products.

The above pure form of acyclovir is a further object of the present invention.

The purification step of the present invention is applicable to every other well known process for the preparation of acyclovir. For example, the above mentioned processes of BE 833.006 and GB 1.567.671 lead to a final product containing from 1 to 3% of guanine, which is a unacceptable amount, since U.S. Pharmacopoeia prescribes a maximum upper limit of 0.7%.

Therefore, the purification of acyclovir as above described, constitutes a further object of the present invention.

The following examples further illustrate the process of the invention.

EXAMPLE 1 a) "Glyoxalguanine" (2)

100 g (0.662 mole) of guanine, 800 ml of $H_2O$ and 150 ml of a 40% w/w glyoxal aqueous solution (1.32 moles) are mixed at room temperature in a 2 l round-bottom flask fitted with condenser, thermometer and magnetic stirrer and the mixture is heated to 80° C. for 4 hours, after which the flask content is gradually cooled to 5° C., filtered and washed with water. After drying under vacuum to constant weight, 136 g of product (98% yield) are obtained, showing a >98% purity by EPLC analysis.

b) $N^2$-Formylguanine (3)

A suspension of 100 g (0.478 mole) of glyoxalguanine in 800 ml of water adjusted to pH 1.8–2.2 with 6 ml of $H_3PO_4$ is added with 107.4 g (0.502 mole) of $NaIO_4$ under mechanic stirring and keeping the temperature within 30° C. with the aid of a water bath, monitoring continuously pH which should not substantially change from 1.8–2.2. The reaction develops a slight, constant hexothermicity until completion, which is obtained about two hours after the addition of the oxidizer. After said time, the reaction mixture is cooled to 5° C., filtered, washed with water and dried. 82 g of formylguanine (3) (96% yield) are obtained, showing a >98% purity by EPLC analysis.

c) $N^2$-formyl-9-(acetoxy)ethoxymethylguanine (4, with $R=CH_3$)

100 g (0.559 mole) of formylguanine (3), 300 g (1.705 moles) of 2-oxa-1,4-diacetoxy-butane and 2 g (0.0105 mole) of p-toluenesulfonic acid are placed into a 500 ml round-bottom flask on an oil bath, fitted with thermometer and a distilling device. The system is brought to depression (30–40 mmHg) and the mass is heated to reach an inner temperature of 118°–122° C. in about 1 hour. Temperature is kept at 118°–122° C. for 8 total hours, distilling the formed acetic acid. The mixture is cooled to 50°–60° C. and diluted with 150 ml of acetone (or n-butyl alcohol or ethyl acetate), cooled to 0°–5° C., filtered and dried under vacuum at 60°–70° C., to obtain 148.3 g of (4) with $R=CH_3$ (90% yield). The elemental analysis and spectroscopic data confirm the suggested structure.

d) Acyclovir (I)

65 g (0.220 mole) of (4) (with $R=CH_3$) are dispersed in 650 ml of a 5% NaOH solution, checking the complete dissolution of the solid. After 12 hour stirring, the mixture is neutralized to pH 5–6 with a HCl aqueous solution. The slurry is cooled to 20°–25° C., the cake is filtered and washed with 400 ml of deionized water. After drying under vacuum at 60°–70° C., 46.1 g of acyclovir (I) are obtained in a 93% yield.

EXAMPLE 2 a) 9-(2-Acetoxy)ethoxymethyl-quanine (6)

300 ml of 95% EtOH, 29.5 g (0.1 mole) of intermediate(4) and 40.4 g (0.4 mole) of $Et_3N$ are placed into a 500 ml round-bottom flask fitted with thermometer, stirrer and bubble condenser. The mass is refluxed for 5 hours. pH is adjusted to 5–6 with aqueous HCl, the mixture is cooled to 15°–20° C., the cake is filtered and washed with 200 ml of deionized water. After drying under vacuum at 60°–70° C., 22.8 g of (6) (85% yield) are obtained.

b) Acyclovir (I)

26.7 g (0.1 mole) of (6) are treated with 5% NaOH, as described in Example 1 d). Acyclovir is obtained in a susbtantially quantitative yield.

EXAMPLE 3

The procedure of Example 1 is followed using, instead of 2-oxa-1,4-diacetoxybutane, a corresponding amount of 2-oxa-1,4-diformyloxy-butane or 2-oxa-1,4-dibenzoyloxy-butane for the alkylation of $N^2$-formylguanine. The corresponding intermediates (4) with R=H and, respectively, with R=phenyl are obtained, substantially in the same yields as those of Example 1c), from which intermediates acyclovir is easily obtained according to what described in Example 1d).

EXAMPLE 4

87.5 g (125 ml, apparent d-0.7) of strong basic resin (AMBERLITE IRA-400) were suspended in deionized water and loaded into a chromatographic column (diameter=4 cm, h=40 cm). After the usual regeneration treatments (subsequent elution with 2M NaOH, 2M HCl, 2M NaOH and deionized water till neutrality) a solution obtained by dissolving 50 g of acyclovir into 100 ml of a 10% NaOH solution, diluted up to 200 ml with water, was loaded. The solution was then eluted with a flow of 250 ml/hour (4.2 ml/min). After eluting the above solution, the column was eluted with the same flow rate with 900 ml of a 1:1 v/v MeOH/1M NaOH mixture. The so obtained eluate was adjusted to pH 5–6 with aqueous HCl. The precipitated solid was filtered, washed with water and dried. 45 g of acyclovir (90% yield) free from guanine were obtained.

We claim:

1. A process for the preparation of 9-(2-hydroxy) ethoxymethyl-guanine (acyclovir) (I):

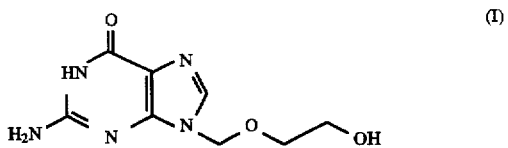

characterized in that $N^2$-formylguanine (3) is subjected to alkylation with 2-oxa-1,4-diacyloxybutane and in that the resulting $N^2$-formyl-9-(2-acyloxy)ethoxymethyl-guanine (4) is hydrolysed, according to the scheme:

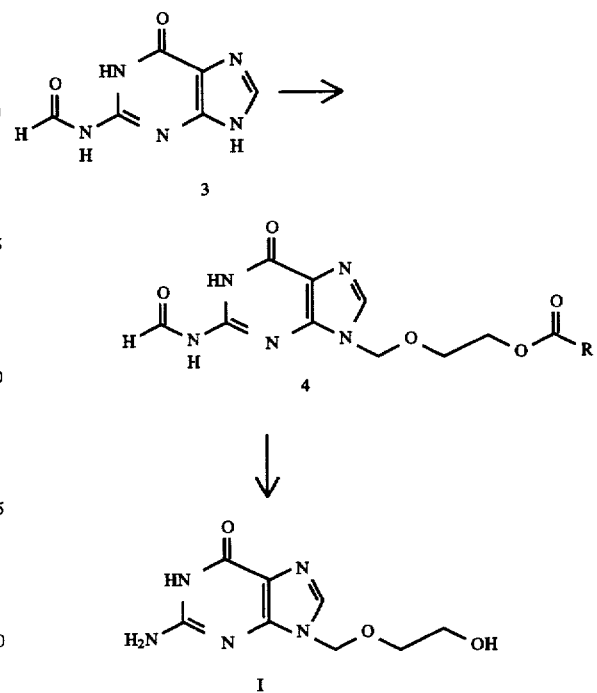

wherein R is hydrogen, $C_1$–$C_4$ alkyl or phenyl.

2. A process according to claim 1, characterized in that the intermediate (4) is at the same time deformylated and O-deacylated by treatment with aqueous NaOH.

3. A process according to claim 1, characterized in that the intermediate (4) is first deformylated with triethylamine in ethanol, and in that the resulting 9-(2-acyloxy) ethoxymethylguanine is hydrolysed to acyclovir with diluted aqueous NaOH.

4. A process according to claim 1, characterized in that $N^2$-formylguanine is prepared by direct formylation of guanine with formic acid or formylacetic anhydride.

5. A process according to claim 1, characterized in that acyclovir is subjected to a purification step which comprises:

a. dissolving acyclovir into an aqueous basic solution and diluting the so obtained solution with water;

b) loading said diluted solution of point a) on a strong anionic ion exchanging column in a resin:acyclovir w/w ratio ranging from 2 to 1.5;

c) eluting said diluted solution at a flow ranging from 200 to 300 ml/hour;

d) eluting acyclovir with an eluant consisting of a mixture formed by lower alcohol/aqueous base solution in a v/v ratio ranging from 0.8 to 1.2, and with a eluant/acyclovir v/w ratio ranging from 15:1 to 20:1 l/kg at the same flow as point c) to give an eluate;

e) isolating acyclovir from said eluate of point d).

6. A process according to claim 5, characterized in that 9-(2-hydroxy)ethoxymethyl-guanine (acyclovir) is obtained substantially free from guanine.

7. A process of claim 5 characterized in that 9-(2-hydroxy)ethoxymethyl-guanine (acyclovir) is obtained with a content of less than 0.1% of guanine.

* * * * *